United States Patent
Sadasivan Vijayakumari et al.

(10) Patent No.: US 8,754,277 B2
(45) Date of Patent: *Jun. 17, 2014

(54) PROCESS FOR PREPARING ETHYLENE AND/OR PROPYLENE

(75) Inventors: Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,298

(22) Filed: Sep. 7, 2012

(65) Prior Publication Data

US 2013/0245293 A1 Sep. 19, 2013

(30) Foreign Application Priority Data

Sep. 7, 2011 (EP) .................................. 11180337

(51) Int. Cl.
*C07C 2/00* (2006.01)

(52) U.S. Cl.
USPC ............ 585/326; 585/324; 585/640; 549/523

(58) Field of Classification Search
USPC ........... 549/513, 523; 585/324, 326, 639, 640
See application file for complete search history.

(56) References Cited

U.S. PATENT DOCUMENTS

| | | | |
|---|---|---|---|
| 4,567,029 A | 1/1986 | Wilson et al. | |
| 4,868,342 A | 9/1989 | Verson | |
| 6,159,433 A | 12/2000 | Chodorge et al. | |
| 6,235,954 B1 * | 5/2001 | Wu et al. | 585/260 |
| 7,238,846 B2 * | 7/2007 | Janssen et al. | 585/640 |
| 7,402,718 B2 * | 7/2008 | Janssen et al. | 585/638 |
| 8,049,054 B2 * | 11/2011 | Chewter et al. | 585/643 |
| 8,269,056 B2 * | 9/2012 | Van Westrenen et al. | 585/639 |
| 8,507,742 B2 * | 8/2013 | Chewter et al. | 585/324 |
| 2007/0155999 A1 | 7/2007 | Pujado et al. | |
| 2007/0203380 A1 | 8/2007 | Vora et al. | |

FOREIGN PATENT DOCUMENTS

| | | |
|---|---|---|
| WO | 2006020083 | 2/2006 |
| WO | 2007135045 | 11/2007 |

OTHER PUBLICATIONS

Hamid, et al.; Handbook of MTBE and Other Gasoline Oxygenates; 1st edition, pp. 65 to 223; 2004.

* cited by examiner

*Primary Examiner* — Golam M M Shameem

(57) ABSTRACT

The present invention provides a process for preparing ethylene and/or propylene, comprising the steps of providing a hydrocarbon stream, comprising C4+ normal olefins and C4+ iso-olefins; converting C4+ isoolefins to tert-alkyl ether and separating the ethers from the hydrocarbon stream; isomersing the C4+ normal olefins to iso-olefins and converting C4+ isoolefins to tert-alkyl ether and separating the ethers from the hydrocarbon stream; converting the obtained tert-alkyl ether to ethylene and propylene by contacting the tert-alkyl ether with a molecular sieve-comprising catalyst and retrieving an olefinic product.

16 Claims, 1 Drawing Sheet

PROCESS FOR PREPARING ETHYLENE AND/OR PROPYLENE

This application claims the benefit of European Application No. 11180337.5 filed Sep. 7, 2011, which is incorporated herein by reference.

FIELD OF THE INVENTION

The invention relates to a process for preparing ethylene and/or propylene.

BACKGROUND TO THE INVENTION

Methanol-to-olefin processes are well described in the art. Typically, methanol-to-olefin processes are used to produce predominantly ethylene and propylene. An example of such a methanol-to-olefin process is described in WO-A 2006/020083. In the process of WO-A 2006/020083, the methanol is first converted into dimethylether (DME) prior to be subjected to a conversion to olefins, thereby reducing the amount of water produced during the conversion to olefins. Both methanol and DME are suitable feedstocks for a Methanol-to-olefin process and therefore such processes are also generally referred to as oxygenate-to-olefin (OTO) processes.

In EP2024303A1, another OTO process is described wherein in addition to oxygenates, also C4 and C5 olefins are provided to the OTO process. These olefins are provided as an olefinic co-feed together with the oxygenates. By providing an olefinic co-feed to the OTO process more ethylene and propylene may be produced. According to EP2024303A1, suitable sources for these olefins are for instance C4 and C5 hydrocarbon fractions obtained from refinery units such as thermal cracking units, catalytic cracking units, steam cracking units, naphtha (steam) cracking units, butadiene extraction units, semi-hydrogenation units for removal of diolefins. Another suitable source for C4 and C5 olefins, disclosed in EP2024303A1, are C4 and C5 olefins which are retrieved from the effluent of the OTO reaction zone. According to EP2024303A1, these C4 and C5 olefins are suitably provided back to the OTO reaction zone as part of a recycle stream to become part of the olefinic co-feed.

However, both the externally provided hydrocarbon fractions as well as the internal recycle stream typically contain paraffinic hydrocarbons which are undesired in the feed to an OTO reaction zone. Paraffins are not converted in the OTO reaction zone and accumulate in the internal recycle. To prevent undesired high levels of paraffins accumulating in the recycle stream, typically part of the recycle stream is purged from the process. However, as part of this purge stream, also valuable olefins are purged from the process.

There is a need in the art to make optimal use of the available olefins to produce ethylene and propylene, while reducing the amount of paraffins provided to the OTO reaction in an OTO process.

SUMMARY OF THE INVENTION

It has now been found that it is possible to provide olefins from the hydrocarbon fractions obtained from refinery units and/or olefins obtained from the effluent of an OTO reaction zone to an OTO reaction zone and to reduce the amount of paraffins provided together with the olefins. This may be achieved by a process wherein iso-olefins are extracted from a hydrocarbon stream comprising iso-olefins and normal olefins by etherification, subsequently isomerising at least part of the remaining normal-olefins to iso-olefins and extracting the newly formed iso-olefins in a further etherification step. The tert-alkyl ethers obtained in the etherification steps may be converted to ethylene and/or propylene in an OTO reaction zone.

Accordingly, the present invention provides a process for preparing ethylene and/or propylene, comprising the steps of:
a) providing a hydrocarbon stream, comprising C4+ normal olefins and C4+ iso-olefins;
b) subjecting the hydrocarbon stream to an etherification process with methanol and/or ethanol wherein at least part of the iso-olefins are converted with methanol and/or ethanol to an tert-alkyl ether, and retrieving a first etherification product stream;
c) separating at least part of the first etherification product stream into at least a first ether-enriched stream and an iso-olefin-depleted hydrocarbon stream;
d) subjecting at least part of the iso-olefin-depleted hydrocarbon stream to an isomerisation process wherein at least part of the normal olefins are isomerised to iso-olefins in the presence of an isomerisation catalyst, and retrieving an iso-olefin-enriched hydrocarbon stream;
e) subjecting at least part of the iso-olefin-enriched hydrocarbon stream to a further etherification process with methanol and/or ethanol wherein at least part of the iso-olefins are converted with methanol and/or ethanol to an tert-alkyl ether, and retrieving a further etherification product stream;
f) separating at least part of the further etherification product stream into at least a further ether-enriched stream and an olefin-depleted hydrocarbon stream;
g) converting at least part of the tert-alkyl ether in the first and/or further ether-enriched stream to ethylene and/or propylene by contacting at least part of the ether-enriched stream with a molecular sieve-comprising catalyst at a temperature in the range of from 350 to 1000° C. and retrieving an olefinic product comprising ethylene and/or propylene.

By converting the iso-olefins in the hydrocarbon stream to tert-alkyl ethers, they can be conveniently separated from the remaining components in the hydrocarbon stream, including components such as paraffins.

In addition, by converting the normal-olefins in the hydrocarbon stream to iso-olefins, the normal-olefins can also be extracted from the hydrocarbon stream as tert-alkyl ethers increasing the fraction of olefins that can be retrieved from the hydrocarbon stream by use of an etherification step.

The process according to the invention can be used to extract olefins from an externally supplied hydrocarbon stream and provide those to an OTO process in the form of tert-alkyl ethers, while it may also be used to extract olefins from a C4+ hydrocarbon fraction that is obtained as part of the effluent of an OTO reaction zone or the effluent of a reaction zone of an olefin cracking process (OCP).

This C4+ hydrocarbon fraction typically contains both olefins and paraffins. By extracting olefins from the C4+ hydrocarbon fraction as tert-alkyl ethers and providing the tert-alkyl ethers as a feed to an oxygenate-to-olefins process, ethylene and/or propylene may be produced. At the same time, the remaining C4+ hydrocarbon fraction, i.e. an olefin-depleted C4+ hydrocarbon fraction may be used for other purposes.

DETAILED DESCRIPTION OF THE INVENTION

Figure 1:
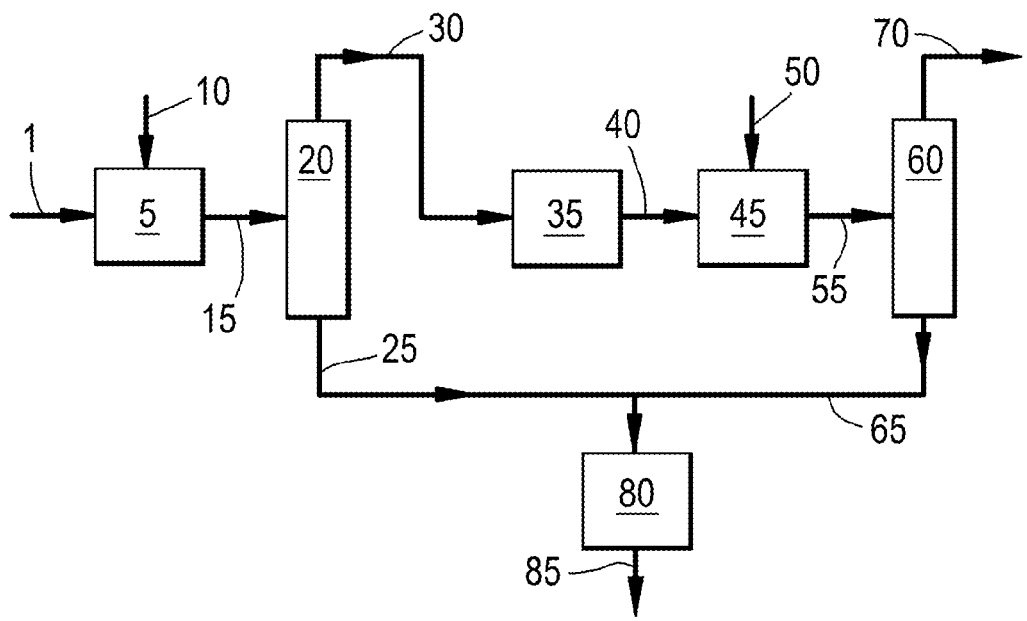
In FIG. 1, a schematic representation of a process according to the invention is provided.

C4+ olefins may suitably be used as part of the feed to an OTO process to produce ethylene and/or propylene. In the process according to the present invention part of the C4+ olefins in a hydrocarbon stream are extracted from the hydrocarbon stream.

In the process according to the invention, C4+ iso-olefins are extracted from the hydrocarbon stream and subsequently C4+ normal olefins in the iso-olefins-depleted hydrocarbon stream are converted to iso-olefins by a skeletal isomerisation process. Following the skeletal isomerisation process, C4+ iso-olefins are again extracted from the now iso-olefins-enriched hydrocarbon stream. The olefins are extracted from the hydrocarbon stream by reacting iso-olefins with an alcohol, in particular methanol and/or ethanol to form tert-alkyl ethers, such as for example methyl tert-butyl ether (MTBE), ethyl tert-butyl ether (ETBE), tert-amyl methyl ether (TAME) or tert-amyl ethyl ether (TAEE). The formed ethers can be separated from the remainder of the hydrocarbon stream.

The tert-alkyl ethers, obtained by extracting the iso-olefins from the C4+ hydrocarbon fraction by reacting the iso-olefins with methanol, are subsequently converted to at least further ethylene and/or propylene in an OTO process. Only iso-olefins, wherein the double bond is located directly adjacent to a tertiary carbon atom can react with methanol to form tert-alkyl ethers. Such iso-olefins are herein referred to as tertiary iso-olefins. Examples of such tertiary iso-olefins include isobutene, 2-methyl-1-butene and 2-methyl-2-butene. An example of an iso-olefin that is not a tertiary iso-olefin is 3-methyl-1-butene.

The process according to the invention is now described in more detail herein below.

In the process according to the invention, a hydrocarbon stream, comprising C4+ normal olefins, for example 1-butene, 2-butene, 1-pentene and/or 2-pentene, and C4+ iso-olefins, for example isobutene, 2-methyl-1-butene or 2-methyl-2-butene and optionally 3-methyl-1-butene, is provided. The hydrocarbon stream may also comprise cyclo-olefins such a cyclopentene. The C5 hydrocarbon-comprising stream may also comprise paraffins, including for instance normal butane and pentane and isobutane and isopentanes.

Preferably, the hydrocarbon stream comprises at least C4 and/or C5 olefins, wherein the term olefins relates to both normal-olefins and iso-olefins, preferably at least C4 olefins. More preferably, the hydrocarbon stream comprises in the range of from 10 to 100 wt % of C4 and/or C5 olefins based on the weight of the olefins in the hydrocarbon stream, preferably of from 50 to 100 wt % of C4 and/or C5 olefins based on the weight of the olefins in the hydrocarbon stream. Even more preferably, the hydrocarbon stream comprises in the range of from 10 to 100 wt % of C4 olefins based on the weight of the olefins in the hydrocarbon stream, preferably of from 50 to 100 wt % of C4 olefins based on the weight of the olefins in the hydrocarbon stream. Optionally, the hydrocarbon stream also contains a diluent. Examples of suitable diluents include, but are not limited to, such as water or steam, nitrogen, argon and methane.

Reference herein to hydrocarbons is to molecules comprising only carbon atoms and hydrogen atoms. Preferably, the hydrocarbon stream comprises in the range of from 10 to 100 wt % of olefins, wherein the term olefins relates to both normal-olefins and iso-olefins, based on the weight of the hydrocarbons in the hydrocarbon stream, preferably of from 60 to 100 wt % of C4 olefins based on the weight of the hydrocarbons in the hydrocarbon stream. Preferably, the hydrocarbon stream comprises in the range of from 1 to 60 wt % of iso-olefins based on the weight of the olefins in the hydrocarbon stream, preferably of from 10 to 50 wt % of iso-olefins based on the weight of the olefins in the hydrocarbon stream. Optionally, the hydrocarbon stream also contains a diluent. Examples of suitable diluents include, but are not limited to, water or steam, nitrogen, argon, C2-C3 paraffins and methane. One example of a suitable hydrocarbon stream is the C4 cut of a FCC effluent stream, which typically contains normal butenes, isobutylene and butanes. Of the C4 cut of an FCC effluent, 20 wt % is isobutylene and the ratio of C4 olefins to C4 paraffins is typically approximately 1.8.

In step (b) of the process according to the invention the hydrocarbon stream is subjected to an etherification process. In the etherification process the hydrocarbon stream is contacted with an alcohol, preferably methanol and/or ethanol, in the presence of a suitable etherification catalyst. When the iso-olefins, preferably isobutylene, 2-methyl-1-butene or 2-methyl-2-butene in the hydrocarbon stream are contacted with the alcohol in the presence of an etherification catalyst, at least part of the iso-olefins are converted with the alcohol to tert-alkyl ethers. Reference herein in to a tert-alkyl ether is to an ether of an alcohol and an iso-olefin. Preferably, the alcohol is methanol and/or ethanol and the tert-alkyl ethers are methyl tert-butyl ether (MTBE), ethyl tert-butyl ether (ETBE), tert-amyl methyl ether (TAME) or tert-amyl ethyl ether (TAEE), which are tert-alkyl ethers of respectively methanol and ethanol with the mentioned iso-olefins. From the etherification process, a first etherification product stream is retrieved. The etherification product stream will comprise the formed tert-alkyl ethers and the remainder of the hydrocarbon stream, i.e. the unreacted components, including C4+ normal-olefins and optionally other hydrocarbons. In addition, the etherification product stream may also comprise unreacted alcohol. Typically the etherification reaction is performed in the presence of an excess of alcohol, i.e. above reaction stoichiometry with the iso-olefin.

At least part, and preferably all, of the first etherification product stream is separated in step (c) into at least an ether-enriched stream and an iso-olefin-depleted hydrocarbon stream, including C4+ normal olefins and optionally other hydrocarbons. The separation of the etherification product stream into an ether-enriched stream and an iso-olefin-depleted hydrocarbon stream can be done with normal separation means provided in the art. Due to the relatively high boiling points of methanol and ethanol, the bulk of the excess of alcohol can be directed toward the ether-enriched stream.

In step (d) of the process according to the present invention, at least part of the iso-olefin-depleted hydrocarbon stream is subjected to an isomerisation process. In this isomerisation process at least part of the C4+ normal olefins in the iso-olefin-depleted hydrocarbon stream undergo skeletal isomerisation to iso-olefins in the presence of an isomerisation catalyst. Following the isomerisation of C4+ normal olefins to iso-olefins, an iso-olefin-enriched hydrocarbon stream is retrieved from step (d).

The iso-olefins formed in step (d) of the process are subsequently extracted from the iso-olefin-enriched hydrocarbon stream by subjecting the iso-olefin-enriched hydrocarbon stream to a further etherification process in step (e) of the process according to the inventions. Similar to the etherification process as described for step (b), in the etherification process of step (e), the hydrocarbon stream is contacted with an alcohol, preferably methanol and/or ethanol, in the presence of a suitable etherification catalyst to convert at least part of the iso-olefins with the alcohol to tert-alkyl ethers. From the further etherification process, a further etherification product stream is retrieved. The further etherification product stream will comprise the formed tert-alkyl ethers and the remainder of the hydrocarbon stream, i.e. the unreacted components, for instance any paraffinic hydrocarbons. In addition, the etherification product stream may also comprise unreacted alcohol.

At least part, and preferably all, of the further etherification product stream is separated in step (f) into at least a further ether-enriched stream and an olefin-depleted hydrocarbon stream, including for instance any paraffinic hydrocarbons. The separation of the further etherification product stream into a further ether-enriched stream and an olefin-depleted hydrocarbon stream can be done with normal separation means provided in the art. Due to the relatively high boiling points of methanol and ethanol, the bulk of the excess of alcohol can be directed toward the ether-enriched stream.

In a preferred embodiment of the process according to the invention, the first and further etherification processes in respectively step (b) and step (e) are combined to a single etherification process. In such an embodiment of the process, at least part of the iso-olefin-enriched hydrocarbon stream obtained in step (d) of the process is provided to the etherification process of step (b) together with or as part of the hydrocarbon stream. The etherification product stream retrieved from stream (b) may be separated in step (c) to obtain a combined ether-enriched stream, i.e. the combination of the first ether-enriched stream and the further ether-enriched stream. The combined ether-enriched steam may be provided to step (g) to convert at least part of the tert-alkyl ether to ethylene and/or propylene.

In this embodiments steps (b) and (e) and steps (c) and (f) are combined, which as the benefit that only one etherification process is required, thereby reducing the process complexity and capex.

In case, at least part of the iso-olefin-enriched hydrocarbon stream is provided to the etherification process of step (b), it is preferred that part of the iso-olefin depleted hydrocarbon stream and/or part of the iso-olefin enriched stream is withdrawn from the process as a purge stream. The advantage of withdrawing part of the iso-olefin depleted hydrocarbon stream and/or part of the iso-olefin enriched stream is that the build-up of paraffins and other hydrocarbon components in the iso-olefin enriched stream is reduced. For instance, paraffins present in the hydrocarbon stream, do not react with the alcohol to from ethers and remain in the hydrocarbon stream. By withdrawing part of the iso-olefin depleted hydrocarbon stream and/or part of the iso-olefin enriched stream from the process, such unreacted paraffins may be removed from the process.

In one preferred embodiment, part of the iso-olefin depleted hydrocarbon stream is withdrawn from the process as purge stream. This has the advantage that the iso-olefin-depleted purge stream may be a valuable stream for further processing. For example a C4 cut of the iso-olefin-depleted purge stream will comprise predominantly 1-butene and 2-butene together with mixed butanes, i.e. normal butane and isobutane. Such a stream is also referred to as Raffinate-2. Raffinate-2 is a chemical building block used in the manufacture of secondary butyl alcohol (SBA) and methyl ethyl ketone (MEK). SBA is an intermediate in the production of industrial cleaning compounds, oil treating chemicals and paint removers, and MEK is an intermediate in the production of surface coatings, adhesives, thinners, printing inks and cleaning agents. In addition, raffinate-2 is a valuable feedstock for olefin metathesis and alkylation processes. In addition it is a suitable feedstock for producing butene-1, which may be used as co-monomer in the production of polyethylene. The C5 cut of the iso-olefin-depleted purge stream is a valuable blend component for the fuel pool. Being depleted in the relatively low boiling iso-olefins, the Reid vapor pressure (RVP) of the C5 cut is lowered compared to the C5 cut of the hydrocarbon stream. As a result, fuel pool RVP increases caused by the addition of low boiling components such as bio-ethanol can be compensated.

In another preferred embodiment, part of the iso-olefin enriched hydrocarbon stream is withdrawn from the process as purge stream. This has the advantage that the iso-olefin-enriched purge stream may be separately subjected to an etherification process with methanol and/or ethanol to extract the iso-olefins in the iso-olefin-enriched purge stream as tert-alkyl ethers. Although, this requires the use of an additional etherification process and unit, this additional etherification process and unit may be much smaller than required for the further etherification process to which the whole of the iso-olefin-enriched hydrocarbon stream is provided instead of only the iso-olefin-enriched purge stream.

Some methanol and/or ethanol may end up in streams other than the ether-enriched streams, such as the iso-olefins-depleted stream, olefin depleted hydrocarbon streams and/or the purge streams. This may be caused for example by the formation of azeotropic mixtures of methanol or ethanol with paraffinic or olefinic hydrocarbon components.

Methanol for instance may form an azeotropic mixture with normal butenes. The methanol concentration in this azeotropic mixture is approximately 4 wt %, based on weight of the azeotropic mixture. The ethanol may also form an azeotropic mixture with the butenes, wherein the ethanol concentration in the azeotropic mixture is approximately 2 wt %, based on weight of the azeotropic mixture. In the case of etherification with a mixed methanol/ethanol stream to produce for instance MTBE and ETBE, there are two different azeotropes. Methanol and ethanol may also form azeotropes with normal butanes and normal pentanes and normal pentenes. The methanol concentration in the azeotropic mixture with C5 normal olefins is approximately 12 wt %, based on weight of the azeotropic mixture. The ethanol concentration in the azeotropic mixture with C5 normal olefins is approximately 8 wt %, based on weight of the azeotropic mixture. The methanol concentration in the azeotropic mixture with normal pentane is approximately 9 wt %.

The iso-olefin-depleted hydrocarbon stream may comprise alcohol. The presence of alcohol in the streams provided to the isomerisation process and further etherification processes will not negatively influence the desired reactions, on the contrary any alcohol provided to a further etherification process as part of and iso-olefin-containing stream will only benefit the etherification process. The presence of alcohol in the iso-olefin-depleted hydrocarbon stream provided to the isomerisation process even has an additional advantageous effect in that it may alkylate normal butane to iso-pentene at temperatures above 300° C., preferably above 350° C. Any tertiary C5 iso-olefins formed by this alkylation may be converted to further tert-alkyl ethers, thereby increasing iso-olefin concentration in the stream provided to the etherification unit and consequently increasing the tert-alkyl ether yield.

However, it may be desired to remove the alcohol from a hydrocarbon stream exiting the process, prior to providing such a stream as feedstock to another process. Alcohols are for instance an undesired component in a feed stream to an alkylation unit. In addition, methanol and ethanol are a valuable feedstock for producing ethylene and propylene and is therefore preferably captured. Alcohol may be extracted from such streams by a water extraction. In one embodiment, alcohol is separated from hydrocarbons in an extraction column. Alcohols and hydrocarbons are fed to the bottom part of the extractor and water to the top section. The column is typically filled with random packing or sieve trays, which enhance alcohol mass-transfer from the hydrocarbon phase to the water phase. Essentially alcohol-free hydrocarbons may be retrieved above the water feed point, and a water/alcohol mixture is the bottom product. The alcohol may separated from the water by distillation and led back to the etherification process, or preferably the water/alcohol mixture may be contacted with a molecular sieve to produce ethylene and/or propylene, for instance by providing the water/alcohol mixture to an OTO unit.

In the process according to the present invention, ethylene and/or propylene are produced in step (g) by converting at least part of the tert-alkyl ethers in the ether-enriched stream to ethylene and/or propylene. At least part of the tert-alkyl ethers in the ether-enriched stream are converted by providing at least part of the ether-enriched stream to a reactor and contacting at least part of the ether-enriched stream with a molecular sieve-comprising catalyst to obtain an olefinic product, comprising ethylene and/or propylene. Preferably, the olefinic product comprises advantageously at least 50 mol %, in particular at least 50 wt %, ethylene and propylene, based on total hydrocarbon content in the olefinic product. In addition, the olefinic product may also comprise C4+ olefins as part of a C4+ hydrocarbon fraction in the olefinic product. The ether-enriched stream is contacted with the molecular sieve-comprising catalyst at a temperature in the range of from 350 to 1000° C., preferably of from 350 to 750° C. When the tert-alkyl ethers, and in particular MTBE and/or ETBE, are contacted with molecular sieves, i.e. the molecular sieve in the molecular sieve-comprising catalyst, the tert-alkyl ethers are at least partially converted to at least ethylene and/or propylene, preferably ethylene and propylene. In addition to ethylene and/or propylene, also C4+ olefins may be formed. As the tert-alkyl ethers are oxygenates, the conversion of the tert-alkyl ethers in the ether-enriched stream may be considered as an OTO process and operated as such an OTO process. Process conditions for operating an OTO process are provided herein below.

In a preferred embodiment of step (g), step (g) comprises contacting an oxygenate-comprising feedstock with the molecular sieve-catalyst and wherein the oxygenate-comprising feedstock comprises tert-alkyl ether obtained in step (b) and/or step (e) and one or more other oxygenates, preferably at least one of methanol and dimethylether, more preferably methanol. Methanol is preferred, in particular when the alcohol used to form the ether is also methanol.

The conversion of oxygenates such as methanol and DME, under such conditions, to olefins in the presence of molecular sieve-comprising catalysts is well known in the art. With respect to the tert-alkyl ethers it is believed, without wishing to be bound to a particular theory, that upon contacting the molecular sieve-catalyst, the tert-alkyl ether decomposes into its corresponding alcohol, i.e. methanol and/or ethanol, and iso-olefin, i.e. isobutene. This decomposition reaction is acid-catalysed. Therefore, preferably the molecular sieve-comprising catalyst comprises acid groups. Some molecular sieves are acidic by nature, whereas other molecular sieve-comprising catalysts comprise binder, support, matrix or other materials comprising acid groups. Even theoretically non-acidic molecular sieves typically comprise some residual acid groups introduced during preparation of the molecular sieve and/or molecular sieve-comprising catalyst. In the absence of any acid groups in the molecular sieve-comprising catalyst it may be preferred to add such groups either by treating the molecular sieve-comprising catalyst to introduce such groups essentially at the surface of the catalyst through impregnation with an acid that resides on the catalyst after calcination, for instance by treating the molecular sieve-comprising catalyst with an acid, such as phosphoric acid, or adding an acid component to catalyst formulation comprising the molecular sieve-comprising catalyst, such as alumina.

Alternatively, the oxygenate-comprising feedstock is contacted with an acid catalyst, prior to contacting the molecular sieve-comprising catalyst. This may for instance be done by passing oxygenate-comprising feedstock through an acid catalyst comprising bed or by passing the feedstock through an acid grid or filter. Preferably, the oxygenate-comprising feedstock is contacted with the acid catalyst at a temperature above 150° C. More preferably, the oxygenate-comprising feedstock is contacted with the acid catalyst at a temperature above 350° C.

Preferably, steam is present as the tert-alkyl ether contacts the catalyst. steam is believed to increase the selectivity of the reaction.

At least part of the alcohol, preferably methanol and/or ethanol, obtained following the decomposition of the tert-alkyl ether is subsequently converted to ethylene and/or propylene over the molecular sieve-comprising catalyst under the process conditions applied. Any residual methanol in the ether-enriched stream is also converted under these conditions.

As mentioned hereinabove it is believed that upon contact with the molecular sieve-comprising catalyst, the tert-alkyl ether decomposes into an alcohol and an isobutene. Depending on the nature of the molecular sieve in the molecular sieve-comprising catalyst, the obtained iso-olefins are either, at least partially, converted to ethylene and/or propylene or remain unconverted.

Any unconverted iso-olefins are retrieved from the process as part of the olefinic product. In addition to any unconverted iso-olefins, the olefinic product may also comprise C4+ olefins as part of a C4+ hydrocarbon fraction produced as by-product in the conversion of oxygenates to ethylene and/or propylene. Preferably, the C4+ olefins in the olefinic product are at least partially converted by contacting, at least part of, the C4+ olefins with a zeolite-comprising catalyst in a further step (h). This can be done by recycling part of C4+ olefins in the C4+ hydrocarbon fraction in the olefinic product to be contacted again with the catalyst in step (g), i.e. in case the molecular sieve-comprising catalyst of step (g) is a zeolite-comprising catalyst. Alternatively, the C4+ olefins in the olefinic product may be converted in a separate unit, reactor or reactor zone downstream of the OTO unit.

The latter is particularly preferred where molecular sieve-comprising catalyst in step (g) comprises at least one SAPO, AlPO, or MeAlPO type molecular sieve, preferably SAPO-34. These catalysts are less suitable for converting iso-olefins. Preferably, the C4+ olefins are contacted with the zeolite-comprising catalyst at a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar). Optionally, the stream comprising C4+ olefins also contains a diluent. Examples of suitable diluents include, but are not limited to, such as water or steam, nitrogen, argon and methane. Under these conditions, at least part of the C4+ olefins is converted to a further olefinic product, comprising ethylene and/or propylene. The further olefinic product may be combined with the olefinic product obtained in step (g). Such a separate process step directed at converting C4+ olefins to ethylene and propylene is also referred to as an olefin cracking process (OCP).

In the process according to the invention, the hydrocarbon stream may be any hydrocarbon stream comprising C4+ normal olefins and C4+ iso-olefins. The hydrocarbon stream may be an external stream providing C4+ olefinic feedstock to the process, however it may also be an internal recycle stream, intended to recycle at least part of a C4+ hydrocarbon fraction from the effluent of the OTO reaction zone or OCP process to be used as a feed to the process in step (g). Examples of external hydrocarbon streams are the C4 and C5 fractions of the effluent of a refinery unit such as thermal cracking units, catalytic cracking units, steam cracking units, naphtha (steam) cracking units, butadiene extraction units and semi-hydrogenation units for removal of C4 and C5 diolefins. A particularly preferred C4 hydrocarbon stream is raffinate-1. Reference herein to raffinate-1 is to a stream comprising of isobutenes, normal butenes and mixed butanes and essentially no butadienes. Reference herein to essentially no butadienes is to a butadiene content of in the range of from 0 to 0.5 wt %, preferably 0 to 0.1, more preferably, 0 to 0.01 wt % of butadienes, based on the weight of the C4 hydrocarbons in the raffinate-1.

In the process according to the invention iso-olefins are reacted with methanol in an etherification process. The etherification process may be any suitable etherification process available in the art for etherifying methanol and iso-olefins to tert-alkyl ethers. Reference is made to the Handbook of MTBE and Other Gasoline Oxygenates, H. Hamid and M. A. Ali ed., $1^{st}$ edition, Marcel Dekker, New York, 2004, pages 65 to 223, where several established process and catalyst for preparing tert-alkyl ethers such as MTBE and ETBE are described. In particular reference is made to chapter 9, pages 203 to 220 of the Handbook of MTBE and Other Gasoline Oxygenates, wherein suitable commercial etherification processes are described. A preferred etherification process is an etherification process wherein the iso-olefins are converted with methanol to a tert-alkyl ether in the presence of a catalyst. Any homogeneous or heterogeneous Brönsted acid may be used to catalyze the etherification reaction. Such catalyst include: sulfuric acid, zeolites, pillared silicates, supported fluorocarbonsulphonic acid polymers and protonated cation-exchange resins catalyst, preferred catalyst are protonated cation-exchange resins catalyst due to the higher catalytic activity and the bound acid sites. A commonly used catalyst is Amberlyst 15.

Preferably, the iso-olefins are converted with an alcohol, preferably methanol and/or ethanol, more preferably methanol, to a tert-alkyl ether at a temperature in the range of from 30 to 100° C., more preferably 40 to 80° C. Preferably, the iso-olefins are converted with methanol and/or ethanol to a tert-alkyl ether at a pressures in the range of from 5 to 25 bar, more preferably 6 to 20 bar.

The iso-olefins may be converted with methanol and/or ethanol to a tert-alkyl ether in any etherification process, however, one preferred etherification process is based on a reactive distillation, which allows for a continuous etherification and separation of the formed ethers.

The hydrocarbon stream preferably contains little to no diolefins. Preferably, the hydrocarbon stream comprises in the range of from 0 to 0.5 wt %, preferably 0 to 0.1, more preferably, 0 to 0.01 wt % of butadienes, based on the weight of the hydrocarbons in the hydrocarbon stream. Most preferably, the hydrocarbon stream does not contain butadiene. Butadienes react to from undesired higher hydrocarbon compounds.

Preferably, the part of the hydrocarbon stream subjected to the first etherification process is selectively hydrogenated to remove at least part of any diolefins, by hydrogenating the diolefins to mono-olefins and/or paraffins, preferably to mono-olefins.

The isomerisation process of step (d) may be any isomerisation process suitable to induce skeletal isomerisation of normal olefins to iso-olefins. Such process are well known in the art and commercially offered by several providers. Preferably, the normal-olefins are isomerised to iso-olefins by contacting the normal olefins with an isomerisation catalyst at a temperature in the range of from 200 to 350° C., preferably in the range of from 250 to 350° C. When the temperature is too low, no or limited skeletal isomerisation will be achieved, while at higher temperatures oligomerisation and/or cracking of the olefins may occur.

Any isomerisation catalyst may be used that catalyses the skeletal isomerisation of normal-olefins to iso-olefins. Preferably, the isomerisation catalyst is a molecular sieve-comprising isomerisation catalyst. More preferably, an isomerisation catalyst comprising at least one of ferrierite, ZSM-22, ZSM-23, ZSM-35, SAPO-5, SAPO-11, SAPO-31, MeAPO-5, MeAPO-11, MeAPO-31, wherein Me is selected from the group of Mg, Mn, Co, Cr, and Fe. These catalyst combine low coke make with high selectivity.

In the present invention, in step (g) an oxygenate-comprising feedstock is converted in an oxygenate-to-olefins process, in which an oxygenate feedstock is contacted in an OTO zone with an oxygenate conversion catalyst under oxygenate conversion conditions, to obtain a conversion effluent comprising lower olefins. Reference herein to an oxygenate feedstock is to an oxygenate-comprising feedstock, including any feedstock comprising at least part of the tert-alkyl ether produced in step (b) and/or step (e). An example of such an oxygenate-comprising feedstock is a feedstock comprising at least part of the ether-enriched stream obtained in step (b) and/or step (e). In the OTO zone, at least part of the feedstock is converted into an olefinic product, i.e. a product containing one or more olefins, including ethylene and/or propylene.

The oxygenate-comprising feedstock comprises at least one tert-alkyl ether, preferably selected from the group of methyl tert-butyl ether (MTBE), ethyl tert-butyl ether (ETBE), tert-amyl methyl ether (TAME) or tert-amyl ethyl ether (TAEE). Other tert-alkyl ethers may be comprised in the feedstock, such as tert-alkyl ethers obtained by the reaction between a C3+ alkyl alcohol and isobutene. Further oxygenates used in step (g) the process according to the invention may preferably be oxygenates, which comprise at least one oxygen-bonded alkyl group. The alkyl group preferably is a C1-C5 alkyl group, more preferably C1-C4 alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenate-comprising feedstock include alcohols and ethers. Examples of preferred oxygenates include alcohols, such as methanol, ethanol, propanol; and dialkyl ethers, such as dimethylether, diethylether, methylethylether. Preferably, the further oxygenate is methanol or dimethylether, or a mixture thereof.

Preferably the oxygenate-comprising feedstock comprises at least 50 wt % of oxygenate, based on total hydrocarbons and oxygenates in the oxygenate-comprising feedstock, more preferably at least 70 wt %.

The oxygenate feedstock can comprise an amount of diluents. During the conversion of the oxygenates, steam is produced as a by-product, which serves as an in-situ produced diluent. Optionally additional steam is added as diluent. The amount of additional diluent that needs to be added depends on the in-situ water make, which in turn depends on the composition of the oxygenate-comprising feed. Where methanol produces 1 mol of water per mol of carbon atoms supplied to the process, MTBE, for example only produces 0.20 mol of water per 1 mol of carbon atoms supplied to the process. Where the diluent is water or steam, the molar ratio of oxygenate to diluent is between 10:1 and 1:20. In case, the oxygenate-comprising feedstock comprises in the range of from 0.01 to 50 wt %, preferably of from 1 to 10 wt %, of tert-alkyl ether, based on the oxygenates in the oxygenate-comprising feedstock, the molar ratio of oxygenate to diluent is preferably in the range of from 3:1 to 1:5, preferably 2:1 to 1:2. In case, the oxygenate-comprising feedstock comprises in the range of from 50 to 100 wt %, preferably 60 to 95 wt %, of tert-alkyl ether, based on the oxygenates in the oxygenate-comprising feedstock, the molar ratio of oxygenate to diluent is preferably in the range of from 1:3 to 1:15, preferably 1:4 to 1:10.

Due to the low in-situ water make of tert-alkyl ethers, the use of diluents other than water may be preferred, in particular when the catalyst is sensitive to hydrothermal deactivation. Other suitable diluents include inert gases such as nitrogen, but may also include paraffins.

Preferably, in addition to the oxygenate, an olefinic co-feed is provided along with and/or as part of the oxygenate feedstock. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon, based on weight of the olefinic co-feed.

Preferably, at least 70 wt % of the olefinic co-feed, during normal operation, is formed by a recycle stream of a C4+ hydrocarbon fraction from the OTO conversion effluent, preferably at least 90 wt % of olefinic co-feed, based on the whole olefinic co-feed, is formed by such recycle stream. In order to maximize production of ethylene and propylene, it is desirable to maximize the recycle of C4 olefins in the effluent of the OTO process. As described herein above, this can be done by recycling at least part of the C4+ hydrocarbon fraction, preferably a C4-C5 hydrocarbon fraction, more preferably C4 hydrocarbon fraction, in the olefinic product, which is retrieved as the OTO effluent. However, a certain part thereof, such as between 1 and 5 wt %, needs to be withdrawn as purge, since otherwise saturated hydrocarbons, in particular C4 saturated hydrocarbons (butane) would build up in the process, which are substantially not converted under the OTO reaction conditions. Preferably, the saturated hydrocarbons are withdrawn from the process using a process according to the present invention wherein at least part of the C4+ hydrocarbon fraction retrieved as the OTO effluent, forms at least part of the hydrocarbon stream provided in step (a).

The preferred molar ratio of oxygenate in the oxygenate feedstock to olefin in the olefinic co-feed provided to the OTO conversion zone depends on the specific oxygenate used and the number of reactive oxygen-bonded alkyl groups therein. Preferably the molar ratio of oxygenate to olefin in the total feed, oxygenate feed and olefinic co-feed, lies in the range of 20:1 to 1:10, more preferably in the range of 18:1 to 1:5, still more preferably in the range of 15:1 to 1:3, even still more preferably in the range of 12:1 to 1:3.

A further advantage of using the selected tert-alkyl ethers as part of the oxygenate-comprising feedstock is that these ethers provide both an oxygenate, being methanol or ethanol, and an olefin, being isobutene, to the process in the form of a single molecule, which decomposes when contacted with the catalyst. This has the advantage that both reactants, i.e. an oxygenate and an olefin, may be provided in a single feed component. For purposes of calculating the molar ratio of oxygenate to olefin in the total feed, the olefins provided to the process as part of the tert-alkyl ether must also be taken into account.

Using the selected tert-alkyl ethers as part of the oxygenate-comprising feedstock allows for instance a more convenient transport of the feedstock, storage of the feedstock and pretreatment of the feedstock. In addition, where C4 olefins are gaseous under ambient conditions, the selected tert-alkyl ethers are liquids under ambient conditions having a significantly higher density than the gaseous C4 olefins. Furthermore, the handling and storage of liquids is less complicated, providing further advantages.

A variety of OTO processes is known for converting oxygenates to an olefin-containing product, as already referred to above. One such process is described in WO-A 2006/020083. Processes integrating the production of oxygenates from synthesis gas and their conversion to light olefins are described in US20070203380A1 and US20070155999A1.

Catalysts suitable for converting the oxygenate-comprising feedstock preferably include molecular sieve-comprising catalyst compositions. Such molecular sieve-comprising catalyst compositions typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing $[TO_4]$ tetrahedral units, more preferably, two or more $[SiO_4]$, $[AlO_4]$ and/or $[PO_4]$ tetrahedral units. These silicon, aluminum and/or phosphorous based molecular sieves and metal containing silicon, aluminum and/or phosphorous based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, -34, -35, -44, but also SAPO-5, -8, -11, -20, -31, -36, -37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48.

Aluminosilicate-comprising catalysts, and in particular zeolite-comprising catalysts, have the additional advantage that in addition to the conversion of methanol or ethanol, these catalysts also induce the conversion of olefins to ethylene and/or propylene. As a result, at least part of the olefins obtained as the tert-alkyl ether is decomposed into methanol or ethanol and the corresponding iso-olefin, may also be converted into ethylene and/or propylene. Furthermore, these aluminosilicate-comprising catalysts, and in particular zeolite-comprising catalysts, are particularly suitable for use as the catalyst in an OCP. Particular preferred catalyst for the OCP reaction, i.e. converting part of the olefins in the second olefinic product, are catalysts comprising at least one zeolite selected from MFI, MEL, TON and MTT type zeolites, more preferably at least one of ZSM-5, ZSM-11, ZSM-22 and ZSM-23 zeolites.

In one preferred embodiment, the molecular sieve in the molecular sieve-comprising catalyst of step (g) is a non-zeolitic molecular sieve, while part of the olefinic product retrieved in step (g), in particular at least part of the C4+ fraction containing olefins, is provided to a subsequent separate OCP unit with a zeolite-comprising catalyst and the C4+ hydrocarbon fraction is at least partially converted by contact with the zeolite-comprising catalyst in a step (h).

Preferred catalysts, for both the OTO reaction in step (g) as well as an optional OCP reaction in step (h), comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80. The oxygenate conversion catalyst can comprise at least 1 wt %, based on total molecular sieve in the oxygenate conversion catalyst, of the molecular sieve having more-dimensional channels, preferably at least 5 wt %, more preferably at least 8 wt %.

Particular preferred catalysts, for both the OTO reaction in step (g) as well as an optional OCP reaction in step (h), include catalysts comprising one or more zeolite having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50% wt of such zeolites based on total zeolites in the catalyst.

In a particularly preferred embodiment the catalyst, for both the OTO reaction in step (g) as well as an optional OCP reaction in step (h), comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst, for both the OTO reaction in step (g) as well as an optional OCP reaction in step (h), may comprise phosphorous as such or in a compound, i.e. phosphorous other than any phosphorous included in the framework of the molecular sieve. It is preferred that an MEL or MFI-type zeolites comprising catalyst additionally comprises phosphorous. The phosphorous may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorous as such or in a compound in an elemental amount of from 0.05-10 wt % based on the weight of the formulated catalyst. A particularly preferred catalyst comprises phosphor-treated MEL or MFI-type zeolites having SAR of in the range of from 60 to 150, more preferably of from 80 to 100. An even more particularly preferred catalyst comprises phosphor-treated ZSM-5 having SAR of in the range of from 60 to 150, more preferably of from 80 to 100.

It is preferred that molecular sieves in the hydrogen form are used in the oxygenate conversion catalyst in step (g), e.g., HZSM-22, HZSM-23, and HZSM-48, HZSM-5. Preferably at least 50 wt %, more preferably at least 90 wt %, still more preferably at least 95 wt % and most preferably 100 w % of the total amount of molecular sieve used is in the hydrogen form. It is well known in the art how to produce such molecular sieves in the hydrogen form.

The reaction conditions of the oxygenate conversion in step (g) include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Typically the catalyst deactivates in the course of the process, primarily due to deposition of coke on the catalyst. Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the molecular sieve. This applies to both the catalyst used in step (g) of the process as well as the catalyst in the optional step (h) of the process. Also the isomerisation catalyst deactivates in the course of the process, also primarily due to deposition of coke on the catalyst. Conventional catalyst regeneration techniques can be employed to remove the coke.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. If desired, spent oxygenate conversion catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 µm, preferably 50-100 µm.

Both the OTO process of step (g) as the optional OCP process of step (h) may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

In step (g) of the process an olefinic product stream comprising ethylene and/or propylene is retrieved. As described herein above, in step (h) a further olefinic product stream comprising ethylene/and propylene may be obtained. The ethylene and/or propylene may be separated from the remainder of the components in the olefinic products. Preferably the olefinic product and further olefinic product at least partially, and preferably fully, combined prior to separating the ethylene and/or propylene from the remaining components. Where the olefinic product comprises ethylene, least part of the ethylene may be further converted into at least one of polyethylene, mono-ethylene-glycol, ethylbenzene and styrene monomer. Where the olefinic product comprises propylene, at least part of the propylene may be further converted into at least one of polypropylene and propylene oxide.

In the process according to the present invention, the hydrocarbon stream comprising C4+ normal olefins and C4+ iso-olefins is first subjected to an etherification process in step (b) and subsequently the iso-olefin-depleted hydrocarbon stream is subjected to an isomerisation process in step (d) to convert the normal olefins to further iso-olefins. Alternatively, it is also possible to subject the hydrocarbon stream comprising C4+ normal olefins and C4+ iso-olefins directly to an isomerisation process as provided in step (d) to convert the normal olefins to iso-olefins.

DETAILED DESCRIPTION OF THE DRAWINGS

In FIG. 1, a process according to the present invention is schematically represented. In FIG. 1, hydrocarbon stream 1, comprising C4+ normal olefins and C4+ iso-olefins is provided to etherification zone 5, together with methanol 10. In etherification zone 5, hydrocarbon stream 1 is contacted with methanol 10 over an etherification catalyst, such as for instance a protonated cationic-exchange resin. Etherification product 15 is retrieved from etherification zone 5 and provided to separation zone 20, wherein etherification product 15 is separated into ether-enriched stream 25 and iso-olefin-depleted hydrocarbon stream 30. Optionally, zones 5 and 20 are combined into a reactive distillation zone, wherein iso-olefins are reacted with methanol to tert-alkyl ethers, while continuously separating tert-alkyl ether from the reaction mixture. Optionally, zones 5 and 20 allow for the recycle of part of the iso-olefin depleted hydrocarbon stream in case not all of the iso-olefins are converted to tert-alkyl ether in a single pass process.

Iso-olefin-depleted hydrocarbon stream 30 is retrieved from separation zone 20 and provided to skeletal isomerisation zone 35. In skeletal isomerisation zone 35, at least part of the normal olefins in iso-olefin-depleted hydrocarbon stream 30 are subjected to a skeletal isomerisation to iso-olefins in the presence of a isomerisation catalyst, such as for example SAPO-11 or Ferrierite. Iso-olefin-enriched hydrocarbon stream 40 is retrieved from skeletal isomerisation zone 35 and provided to second etherification zone 45, together with methanol 50. In etherification zone 45, iso-olefin-enriched hydrocarbon stream 40 is contacted with methanol 50 over an etherification catalyst, such as for instance a protonated cationic-exchange resin. Further etherification product 55 is retrieved from etherification zone 45 and provided to separation zone 60, wherein etherification product 55 is separated into ether-enriched stream 65 and olefin-depleted hydrocarbon stream 70. Optionally, zones 45 and 60 are combined into a reactive distillation zone, wherein iso-olefins are reacted with methanol to tert-alkyl ethers, while continuously separating tert-alkyl ether from the reaction mixture. Optionally, zones 45 and 60 allow for the recycle of part of the iso-olefin depleted stream in case not all of the iso-olefins are converted to tert-alkyl ether in a single pass process.

Ether-enriched streams 25 and 65 are provided to oxygenate-to-olefin zone 80. In oxygenate-to-olefin zone 80, ether-enriched streams 25 and 65 are contacted with a molecular sieve-comprising catalyst, for example a catalyst comprising ZSM-5, such as a catalyst comprising ZSM-5 and ZSM-23, based on the zeolite content in the catalyst, or a catalyst comprising SAPO-34. Optionally, additional oxygenate, such as methanol or dimethylether, olefins and water are added to oxygenate-to-olefin zone 80 (not shown). Olefinic product 85, comprising ethylene and/or propylene is retrieved from oxygenate-to-olefin zone 80.

Figure 2:
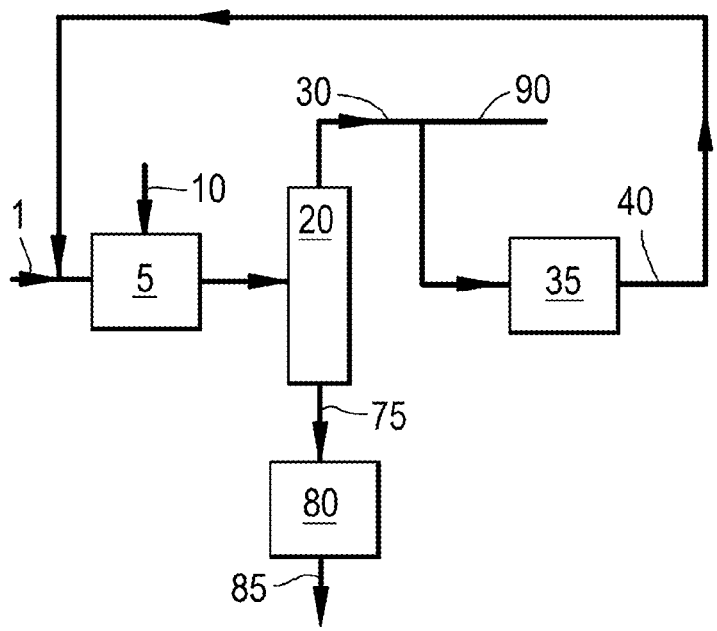
In FIG. 2, another schematic representation of a process according to the invention is provided.

In FIG. 2, a process similar to that of FIG. 1 is represented, however in the process of FIG. 2, etherification zones 45 and accompanying separation zone 60 have been removed. Instead, iso-olefin-enriched stream 40 is recycled and provided to etherification zone 5 together with hydrocarbon stream 1. From separation zone, combined ether-enriched stream 75 is retrieved and provided to oxygenate-to-olefin zone 80. In oxygenate-to-olefin zone 80, ether-enriched streams 25 and 65 are contacted with a molecular sieve-comprising catalyst, for example a catalyst comprising ZSM-5, such as a catalyst comprising 50 wt % of ZSM-5 and 50 wt % ZSM-23, based on the zeolite content in the catalyst, or a catalyst comprising SAPO-34. Optionally, additional oxygenate, such as methanol or dimethylether, olefins and water are added to oxygenate-to-olefin zone 80 (not shown). Olefinic product 85, comprising ethylene and/or propylene, is retrieved from oxygenate-to-olefin zone 80. To prevent the build-up of paraffins in the iso-olefin-enriched hydrocarbon stream 40, part of iso-olefin depleted hydrocarbon stream 30 is withdrawn from the process via purge stream 90. The part of iso-olefin depleted hydrocarbon stream 30 which was withdrawn from the process to purge paraffins from the process may suitably be used as a raffinate-2 feedstock to another process. Alternatively, instead of withdrawing part of iso-olefin depleted hydrocarbon stream 30 as a purge as shown in FIG. 2, it is also possible to withdraw part of iso-olefin-enriched hydrocarbon stream 40 to purge paraffins from the process. It that case, it may be preferred to subject the purge stream to a separate etherification process to extract the iso-olefins in the purge stream.

EXAMPLES

The invention is illustrated by the following non-limiting examples.

Example 1

Several molecular sieves were tested to show their ability to convert MTBE to an olefinic product. To test the molecular sieves for catalytic performance, a powder of the respective molecular sieves was pressed into tablets and the tablets were broken into pieces and sieved. MTBE was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to the reaction temperature and a mixture consisting of 6 vol % MTBE balanced in $N_2$ was passed over the catalyst at atmospheric pressure (1 bar). The Gas Hourly Space Velocity (GHSV) is determined by the total gas flow over the zeolite weight per unit time (ml.gzeolite$^{-1}$.h$^{-1}$). The gas hourly space velocity used in the experiments was 10000 (ml.gzeolite$^{-1}$.h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The effluent from the reactor obtained at several reactor temperatures was analyzed. The results are shown in Table 1.

TABLE 1

| T [° C.] | Catalyst | C2= [wt %] | C3= [wt %] | C4= [wt %] | C5 [wt %] | Light ends [wt %] | C6+ [wt %] | C4 paraffin [wt %] |
|---|---|---|---|---|---|---|---|---|
| 420 | SAPO-34 | 7.90 | 15.15 | 65.43 | 9.18 | 0.19 | 1.06 | 1.09 |
| 525 | SAPO-34 | 9.41 | 18.17 | 50.01 | 14.78 | 1.57 | 2.58 | 3.49 |
| 420 | ZSM-5* | 10.86 | 28.10 | 15.93 | 8.13 | 0.12 | 23.56 | 13.31 |
| 525 | ZSM-5* | 26.77 | 38.11 | 11.46 | 2.69 | 0.03 | 13.01 | 7.92 |
| 525 | ZSM-5# | 17.89 | 39.85 | 25.49 | 3.22 | 1.79 | 9.69 | 2.07 |
| 525 | ZSM-23 | 20.73 | 42.89 | 29.00 | 2.05 | 0.59 | 3.62 | 1.12 |
| 525 | ZSM-22 | 17.19 | 39.88 | 35.52 | 2.12 | 0.44 | 3.99 | 0.86 |

*SAR 80
SAR 280

For all tested catalyst, the conversion of MTBE was complete. No MTBE or methanol was detected in the effluent of the reactor.

The zeolite catalysts, i.e. ZSM-5, ZSM-22 and ZSM-23, show a good conversion of the MTBE, including the isobutene part of the MTBE, to ethylene and propylene. An advantage of the one-dimensional zeolites having 10-membered ring channels, i.e. ZSM-22 and ZSM-23, is the lower paraffin make and C6+ make compared to the multi-dimensional ZSM5 zeolites.

By reducing the SAR of the ZSM-5 catalyst, the ethylene and propylene yield is improved, while significantly less C4 olefins are produced.

% MTBE and 3 vol % methanol, balanced in $N_2$ was passed over the catalyst at atmospheric pressure (1 bar). The Gas Hourly Space Velocity (GHSV) is determined by the total gas flow over the zeolite weight per unit time (ml.gzeolite$^{-1}$.h$^{-1}$). The gas hourly space velocity used in the experiments was 10000 (ml.gzeolite$^{-1}$.h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The results are shown in Table 2.

TABLE 2

| T [° C.] | Catalyst | C2= [wt %] | C3= [wt %] | C4= [wt %] | C5 [wt %] | Light ends [wt %] | C6+ [wt %] | C4 paraffin [wt %] |
|---|---|---|---|---|---|---|---|---|
| 525 | SAPO-34 | 18.11 | 22.08 | 44.94 | 8.23 | 2.94 | 1.64 | 2.05 |
| 525 | ZSM-5* | 25.72 | 37.64 | 11.57 | 3.24 | 0.65 | 13.79 | 7.41 |
| 525 | ZSM-5# | 17.66 | 42.42 | 20.31 | 3.31 | 1.82 | 12.88 | 1.61 |
| 525 | ZSM-23 | 21.45 | 46.66 | 21.09 | 2.77 | 0.81 | 6.16 | 1.06 |
| 525 | ZSM-22 | 17.84 | 48.46 | 24.30 | 2.61 | 0.83 | 5.24 | 0.71 |

*SAR 80
SAR 280

The non-zeolite SAPO-34 catalyst shows a low paraffin make and C6+ make, however is less suitable for converting iso-C4 olefins as can be seen from the relative high C4 olefin content in the effluent of the reactor. These C4 olefins are preferably subsequently converted in an OCP reactor over a zeolite catalyst. It will be clear from table 1, that zeolite catalyst show a better conversion of C4 olefins to the desired ethylene and propylene products. Increasing the reaction temperature, results in a reduction of the C4 olefin content in the effluent of the reaction.

Example 2

Several molecular sieves were tested to show their ability to convert a mixture of MTBE and methanol to an olefinic product. To test the molecular sieves for catalytic performance, a powder of the respective molecular sieves was pressed into tablets and the tablets were broken into pieces and sieved. A mixture of MTBE and methanol was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to 525° C. and a mixture consisting of 3 vol The zeolite catalysts do not show a significant change in the obtained C2 to C4 olefinic product slate, when methanol is added to the MTBE feed. As a result, it can be expected that for an existing methanol based OTO process using a zeolite catalyst, MTBE can be blended into the methanol feed without requiring significant changes to the process operation. In case of the SAPO-34 catalyst, the ratio of propylene to ethylene obtained when using only MTBE as a feed is higher than the ratio obtained from a feed comprising a mixture of MTBE and methanol. As a result it can be concluded that blending MTBE into a methanol feedstock to a SAPO-34 based OTO process will result in an improved ratio of propylene to ethylene without requiring significant changes to the process operation.

What is claimed is:

1. A process for preparing ethylene and/or propylene, comprising the steps of:
   a) providing a hydrocarbon stream, comprising C4+ normal olefins and C4+ iso-olefins;
   b) subjecting the hydrocarbon stream to an etherification process with methanol and/or ethanol wherein at least part of the iso-olefins are converted with methanol and/or ethanol to an tert-alkyl ether, and retrieving a first etherification product stream;
   c) separating at least part of the first etherification product stream into at least a first ether-enriched stream and an iso-olefin-depleted hydrocarbon stream;

d) subjecting at least part of the iso-olefin-depleted hydrocarbon stream to an isomerisation process wherein at least part of the normal olefins are isomerised to iso-olefins in the presence of an isomerisation catalyst, and retrieving an iso-olefin-enriched hydrocarbon stream;

e) subjecting at least part of the iso-olefin-enriched hydrocarbon stream to a further etherification process with methanol and/or ethanol wherein at least part of the iso-olefins are converted with methanol and/or ethanol to an tert-alkyl ether, and retrieving a further etherification product stream;

f) separating at least part of the further etherification product stream into at least a further ether-enriched stream and an olefin-depleted hydrocarbon stream;

g) converting at least part of the tert-alkyl ether in the first and/or further ether-enriched stream to ethylene and/or propylene by contacting at least part of the ether-enriched stream with a molecular sieve-comprising catalyst at a temperature in the range of from 350 to 1000° C. and retrieving an olefinic product comprising ethylene and/or propylene.

2. A process according to claim 1, wherein steps (b), (e) and steps (c) and (f) are combined by providing at least part of the iso-olefin-enriched hydrocarbon stream obtained in step (d) to the etherification process of step (b) together with or as part of the hydrocarbon stream to obtain a combined ether-enriched stream, which is provided to step (g).

3. A process according to claim 1, wherein the olefinic product further comprises C4 olefins and wherein the process comprises the further steps:

h) contacting at least part of the C4 olefins in the olefinic product with a zeolite-comprising catalyst at a temperature in the range of from 350 to 1000° C. and converting at least part of the olefinic product into a further olefinic product comprising ethylene and/or propylene.

4. A process according to claim 3, wherein the zeolite-comprising catalyst comprises at least one zeolite selected from MFI, MEL, TON and MTT type zeolites.

5. A process according to claim 3, wherein the molecular sieve-comprising catalyst comprises at least one SAPO, AlPO, or MeAlPO type molecular sieve.

6. A process according to claim 4, wherein the molecular sieve-comprising catalyst comprises at least one SAPO, AlPO, or MeAlPO type molecular sieve.

7. A process according to claim 1, wherein in step (g) comprises contacting an oxygenate-comprising feedstock with the molecular sieve-catalyst and wherein the oxygenate-comprising feedstock comprises tert-alkyl ether obtained in step (b) and/or step (e) and one or more other oxygenates, preferably at least one of methanol and dimethylether.

8. A process according to claim 1, wherein the normal-olefins are isomerized to iso-olefins by contacting the normal olefins to with an isomerisation catalyst at a temperature in the range of from 200 to 350° C.

9. A process according to claim 1, wherein the isomerisation catalyst is a molecular sieve-comprising isomerisation catalyst.

10. A process according to claim 1, wherein the iso-olefins are converted with methanol and/or ethanol to the tert-alkyl ether by contacting the iso-olefin with methanol and/or ethanol in the presence of an etherification catalyst at a temperature in the range of from 30 to 100° C.

11. A process according to claim 10, wherein the etherification catalyst is a protonated cation-exchange resin catalyst.

12. A process according to claim 1, wherein in step (b) and (e) iso-olefins are converted with methanol to MTBE.

13. A process according to claim 1, wherein the hydrocarbon stream comprises less than 0.5 wt % of diolefins, based on the weight of the hydrocarbons in the hydrocarbon stream.

14. A process according to claim 1, wherein the hydrocarbon stream comprises C4 olefins and/or C5 olefins.

15. A process according to claim 1, wherein the olefinic product comprises ethylene and at least part of the ethylene is further converted into at least one of polyethylene, monoethylene-glycol, ethylbenzene and styrene monomer.

16. A process according to claim 1, wherein the olefinic product comprises propylene and at least part of the propylene is further converted into at least one of polypropylene and propylene oxide.

* * * * *